United States Patent [19]
Frank et al.

[11] Patent Number: 5,374,188
[45] Date of Patent: Dec. 20, 1994

[54] ELECTRO-SURGICAL INSTRUMENT AND METHOD FOR USE WITH DENTAL IMPLANTATIONS

[75] Inventors: Milton Frank, Riverdale, N.Y.; Joel L. Rosenlicht, Manchester, Conn.

[73] Assignee: BEI Medical Systems, Inc., Hackensack, N.J.

[21] Appl. No.: 93,273

[22] Filed: Jul. 19, 1993

[51] Int. Cl.$^5$ .............. A61C 3/00; A61C 19/00; A61C 5/00; A61B 17/39
[52] U.S. Cl. .................. 433/32; 433/215; 606/45; 606/49
[58] Field of Search .......... 433/32, 144, 215; 606/45, 49

[56] References Cited

U.S. PATENT DOCUMENTS

| | | | |
|---|---|---|---|
| 1,794,296 | 2/1931 | Hyams | 606/45 |
| 1,919,543 | 7/1933 | Doane | 606/49 |
| 1,930,214 | 10/1933 | Wappler | 174/89 |
| 3,821,513 | 6/1974 | Christensen | 433/32 X |
| 4,153,060 | 5/1979 | Korostoff et al. | 433/32 X |
| 4,481,948 | 11/1984 | Sole | 606/45 |
| 4,688,569 | 8/1987 | Rabinowitz | 606/45 X |
| 4,917,082 | 4/1990 | Grossi et al. | 606/49 X |
| 5,064,424 | 11/1991 | Bitrolf | 606/46 |
| 5,133,713 | 7/1992 | Huang et al. | 606/46 |

*Primary Examiner*—Gene Mancene
*Assistant Examiner*—Nicholas D. Lucchesi
*Attorney, Agent, or Firm*—Malina & Wolson

[57] ABSTRACT

An electro-surgical instrument and method is described for exposing gingival areas in preparation for a dental implant. The instrument includes an elongated handle, a leg extending perpendicular to the handle adjoined therewith, and a circular cutting loop. The loop is defined by a plane perpendicular to the leg and tangentially attached thereto along a circumference of the loop. The loop is formed of a unitary electrically conductive wire such as tungsten, and extends into the leg and at least partially into the handle. A high frequency current is passed through the wire into the loop to best activate the latter for cutting the gingival areas.

15 Claims, 1 Drawing Sheet

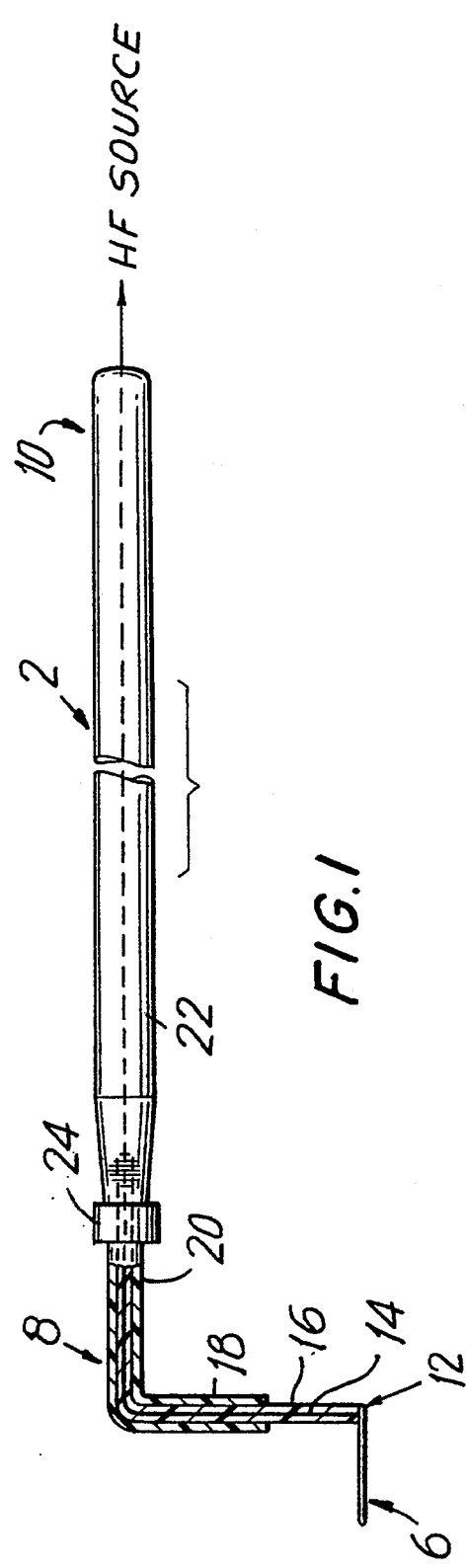
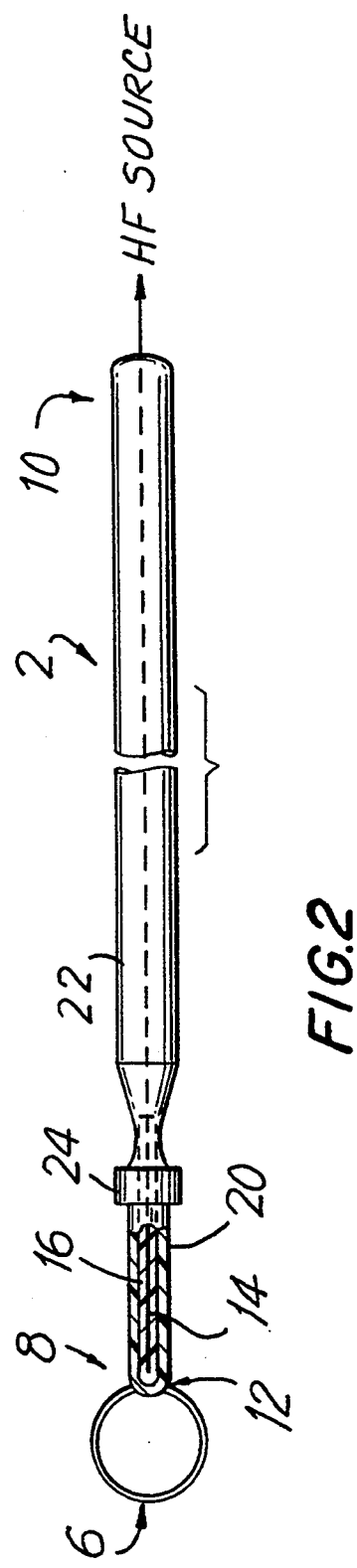

ELECTRO-SURGICAL INSTRUMENT AND METHOD FOR USE WITH DENTAL IMPLANTATIONS

BACKGROUND OF THE INVENTION

1. Field of the Invention

The invention relates to an electro-surgical instrument having at one end a cutting electrode activated by a high frequency current source and specifically designed for cutting a core of gingiva precedent to implantation of a dental post.

2. The Related Art

The general art of electro-surgery has been practiced for most of this century. Therein a very high frequency but relatively low voltage current, i.e. radio frequency, has been harnessed for surgical cutting purposes. Usually, the patient is adapted to be electrically connected with one terminal of a high frequency current source while the scalpel is connected to an active electrode and serves as the opposite terminal. The high frequency current, when applied to the patient's tissue, induces a localized overheating. Colloidal matter is thereby caused to precipitate from the tissue cells. This surgery does not burn but rather sears the tissue to an extent sufficient to prevent bleeding. Hence, the procedure often has been termed "bloodless surgery".

Different areas of the human body represent different surgical challenges. Uniquely configured instruments are often necessary to meet these challenges. For instance, U.S. Pat. No. 1,930,214 (Wappler) describes a surgical electrode for use in combination with an endoscopic tube within interior areas of a body cavity. The electrode is in the form of a pair of conducting wire diverging from the forward end of a handle. An operative conductive loop, which performs the cutting, extends from the pair of diverging wires and defines a plane substantially transverse to the axis of the handle. U.S. Pat. No. 1,963,636 (Wappler) discloses a further improvement of this technology wherein the loop is movable by a guiding or camming device relative to the endoscope.

U.S. Pat. No. 1,919,543 (Doane) is concerned with an improved method of removing tonsillar tissue. Instead of grounding the patient's body to a different electrode, the two electrodes are placed near each other with little intervening tissue. Under FIG. 3 is illustrated one possible type of electrode in the form of a ring which collars the tonsil. Once collared, an active essentially straight tipped electrode is brought in contact with the now grounded tonsil.

U.S. Pat. No. 4,481,948 (Sole) is concerned with a method and instrument for performing extracapsular cataract surgery. The electrode wire portion contacting the eye is a closed loop tangentially supported by an elongated stem portion with a substantially right angular bend. The stem at an opposite end of the right angular bend is attached through an obtuse angular bend to a lower end of a handle.

U.S. Pat. No. 4,917,082 (Grossi et al) reports an electrode for use with a urological endoscope. A stabilizer is provided which allows the electrode to be resiliently snapped onto the telescope. A U-shaped tungsten wire loop serves as the active end of the electrode. The loop has integral space parallel wire arms which extend upward toward the telescope.

U.S. Pat. No. 5,064,424 (Bitrolf) is concerned with a cutting instrument designed for endoscopic operation in the rectum. The described instrument solves the problem of switching between coagulation and resection electrode instruments. Quicker and safer operation is performed through a closed loop annular portion electrode tangentially held on a sectioning face of a part-spherical portion of an electrode.

None of the aforementioned art has addressed the problem of gingival surgery required in conjunction with dental implantations. Indeed, the aforementioned art has not even suggested the use of electro-surgical devices for operating on the gingiva. The very nature of the problem requires an instrument which guarantees that only the correct amount of gingiva is destroyed or removed, and conductive damage to tissue is negligible.

Accordingly, it is an object of the present invention to provide a method for operating on gingiva to remove or destroy the correct amount thereof pursuant to installing a dental post.

It is another object of the present invention to provide an electro-surgical instrument of the correct shape and size for guaranteeing that only the correct amount of gingiva is destroyed or removed pursuant to a dental implantation.

SUMMARY OF THE INVENTION

An electro-surgical instrument for exposing gingival areas in preparation for a dental implant is provided which includes:

(i) an elongated handle with a first and second end;
(ii) a leg extending perpendicularly to the handle and joined therewith at the first end; and
(iii) a circular cutting loop oriented in a plane perpendicular to the leg, a distal end of the leg opposite the first end being tangentially joined at a right angle to the loop along a circumference thereof, the loop being formed of a unitary electrically conductive wire that extends into the leg and at least partially into the handle; and wherein the electrically conductive wire is activated by passing a current therethrough.

Advantageously, the loop is formed of tungsten wire. The wire may have a diameter of about 0.0005 to about 0.01 inches, preferably being about 0.002 inches. The loop has a diameter smaller than a length of the leg which, in turn, is smaller than a length of the handle. An electrically insulating sheath will surround the electrically conductive wire along at least a portion of the leg. Coaxially surrounding the sheath can be a perfluoropolyethylene (TEFLON®) tubing. Preferably the TEFLON® covers no more than 80% of the length of the leg, optimally between 10–50% of a length of the leg. The TEFLON® tubing may also cover as an outer layer a length of the handle near a first end thereof; the covering will usually be less than 10% of the handle length, optimally between about 1 and 5% thereof.

The handle is formed of a stem and a gripping section. The ends are connected by a coupling mechanism such as a heat shrinkable tubular plastic outer covering coaxial with the handle.

The invention also provides a method for exposing gingival areas in preparation for a dental implant including the steps of contacting the gingiva with an instrument comprising:

(i) an elongated handle with a first and second end;
(ii) a leg extending perpendicularly to the handle and joined therewith at the first end; and (iii) a circular cutting loop oriented in a plan perpendicular to the leg, a distal end of the leg opposite the first end being tangentially joined at a right angle to the loop along a circumference thereof, the loop being formed of a unitary electrically conductive wire that extends into the leg and at least partially into the handle; and including the step of passing a current through the electrically conductive wire thereby heating the loop which contacts the gingiva.

BRIEF DESCRIPTION OF THE DRAWING

The above features, advantages and objects of present invention will more fully be appreciated through the following detailed discussion, reference being made to the drawing consisting of:

FIG. 1 which is a partially cut-away elevational view of the instrument;

FIG. 2 is a partially cut-away top plan view of the instrument.

DETAILED DESCRIPTION

The electro-surgical instrument of the present invention as shown in FIGS. 1 and 2 includes an elongated handle 2, a leg 4 and a circular cutting loop 6. Handle 2 has a first and second end 8 and 10. Leg 4 extends perpendicular to the first end 8 of the handle.

The circular cutting loop 6 is defined by a plane perpendicular to leg 4. A distal end 12 of the leg 4, which is opposite first end 8, is tangentially joined at a right angle to loop 6 along a circumference thereof. Loop 6 is formed of a unitary electrically conductive wire 14, best formed from tungsten, that extends into the leg and at least partially into the handle. Wire 14 has a thickness of about 0.002 inches. Loop 6 has a diameter smaller than a length of the leg which, in turn, is smaller than a length of the handle.

An electrically insulating sheath 16 surrounds wire 14 along at least a part of leg 4. Coaxially surrounding sheath 16 is tubing 18 formed of perfluoropolyethylene, e.g. TEFLON ®. Tubing 18 covers no more than about 80% of a length of the leg 4, preferably no more than 50%. Tubing 18 is coaxially formed as an outer layer along less than 10% of the length of handle 2 and covers first end 8 thereof, preferably between 1 and 5% thereof.

The handle is comprised of a stem section 20 and a gripping section 22. These sections are connected, at least in part, by a heat shrinkable tubular plastic outer covering 24 coaxial with the handle 2. Stem and gripping sections 20 and 22 form the respective first and second ends 8 and 10 of the handle. The wire 14 proceeds through handle 2 from which it can be connected to a high frequency electrical source.

The method according to the present invention involves contacting a gingival area with loop 6 through which a high frequency electrical source is being pulsed. Loop 6 upon contact cuts a core of gingiva exactly the correct size for installing a dental implant onto its post. It is to be understood that the method of the present invention contemplates application of the electrically heated loop either before or after insertion of a post upon which the dental implant is anchored. Of course, the primary method utilizes the loop for contacting the gingiva after the post is installed. Secondarily, the heated loop may be used preparatory to its installation of the post.

It should be understood that the foregoing description is only illustrative of the invention. Various alternatives and modifications can be devised by those skilled in the art without departing from the invention. Accordingly, the present invention is intended to embrace all such alternatives, modifications and variations which fall within the scope and purview of the appended claims.

What is claimed is:

1. An electro-surgical instrument for exposing gingival areas in preparation for a dental implant, comprising:
   (i) an elongated handle with a first and second end;
   (ii) a leg extended perpendicular to said handle and joined therewith at said first end;
   (iii) a circular cutting loop oriented in a plane perpendicular to said leg, a distal end of said leg opposite said first end being tangentially joined at a right angle to said loop along a circumference thereof, said loop being formed of a unitary electrically conductive wire that extends into said leg and at least partially into said handle.

2. An instrument according to claim 1 wherein said loop is formed of tungsten.

3. An instrument according to claim 2 wherein the wire has a diameter of about 0.0005 to about 0.01 inches.

4. An instrument according to claim 3 wherein the wire has a diameter of about 0.002 inches.

5. An instrument according to claim 1 wherein said loop has a diameter smaller than a length of said leg which, in turn, is smaller than a length of said handle.

6. An instrument according to claim 1 wherein said wire along at least a part of said leg is surrounded by an electrically insulating sheath.

7. An instrument according to claim 6 wherein said sheath is coaxially surrounded by perfluoropolyethylene tubing.

8. An instrument according to claim 7 wherein said tubing covers no more than 80% of the length of said leg.

9. An instrument according to claim 8 wherein said tubing is coaxially formed as an outer layer along less than 10% of the length of said handle and covers said first end thereof.

10. An instrument according to claim 9 wherein said outer layer of said tubing covers between about 1 and 5 percent of said length of said handle.

11. An instrument according to claim 7 wherein said tubing covers no more than 50% of the length of said leg.

12. An instrument according to claim 1 wherein said handle comprises a stem section and a gripping section, said sections being connected by a coupling means.

13. An instrument according to claim 12 wherein said stem section and gripping section form said respective first and second ends.

14. An instrument according to claim 12 wherein a heat shrinkable tubular outer covering coaxial with said handle forms said coupling means.

15. A method for exposing gingival areas in preparation for a dental implant comprising the steps of:
   readying for surgery an instrument comprising:
   (i) an elongated handle with a first and second end;
   (ii) a leg extended perpendicular to said handle and joined therewith at said first end;
   (iii) a circular cutting loop oriented in a plane perpendicular to said leg, a distal end of said leg opposite said first end being tangentially joined at a right angle to said loop along a circumference thereof, said loop being formed of a unitary electrically conductive wire that extends into said leg and at least partially into said handle; and
   passing an electric current through said electrically conductive wire to heat activate said loop;
   contacting the gingiva with said heat activated loop.

* * * * *